(12) United States Patent
Cheng et al.

(10) Patent No.: US 12,171,870 B2
(45) Date of Patent: *Dec. 24, 2024

(54) CONTACT LENS PACKAGING SOLUTIONS

(71) Applicant: ALCON INC., Fribourg (CH)

(72) Inventors: Jing Cheng, Brea, CA (US); Stephen Raymond Perreault, Peachtree Corners, GA (US); Daqing Wu, Suwanee, GA (US); Steve Yun Zhang, Sugar Hill, GA (US); Jang-Shing Chiou, Suwanee, GA (US)

(73) Assignee: Alcon Inc., Fribourg (CH)

( * ) Notice: Subject to any disclaimer, the term of this patent is extended or adjusted under 35 U.S.C. 154(b) by 532 days.

This patent is subject to a terminal disclaimer.

(21) Appl. No.: 17/392,425

(22) Filed: Aug. 3, 2021

(65) Prior Publication Data

US 2022/0047502 A1 Feb. 17, 2022

Related U.S. Application Data

(60) Provisional application No. 63/064,093, filed on Aug. 11, 2020.

(51) Int. Cl.
| | | |
|---|---|---|
| *A61K 9/00* | (2006.01) | |
| *A45C 11/00* | (2006.01) | |
| *A61K 9/51* | (2006.01) | |
| *A61K 31/685* | (2006.01) | |
| *A61L 12/04* | (2006.01) | |
| *B65B 25/00* | (2006.01) | |

(52) U.S. Cl.
CPC .......... *A61K 9/0051* (2013.01); *A45C 11/005* (2013.01); *A61K 9/5115* (2013.01); *A61K 9/5192* (2013.01); *A61K 31/685* (2013.01); *A61L 12/04* (2013.01); *B65B 25/008* (2013.01)

(58) Field of Classification Search
CPC .. A61K 9/0051; A61K 9/5146; A61K 9/5192; A61K 31/685; A45C 11/05; A61L 12/04; B65B 25/008; B29D 11/00096; G02B 1/043

See application file for complete search history.

(56) References Cited

U.S. PATENT DOCUMENTS

| | | |
|---|---|---|
| 4,818,537 A | 4/1989 | Guo |
| 9,575,332 B2 | 2/2017 | Qiu et al. |
| 2017/0119811 A1 | 5/2017 | Klein et al. |

FOREIGN PATENT DOCUMENTS

| | | |
|---|---|---|
| CN | 101657204 A | 2/2010 |
| WO | 2008059501 A2 | 5/2008 |
| WO | 2015004466 A1 | 1/2015 |

OTHER PUBLICATIONS

Pitt et al, Loading and Release of Phosphatidylcholine from Contact Lenses, Optometry and Vision Science, col. 88, No. 4, pp. 502-506 (Year: 2011).*

Lum Edward et.al.: "Osmolality and buffering agents in soft contact lens packaging solutions", Contact Lens and Anterior Eye, vol. 27, No. 1, Mar. 1, 2004, pp. 21-26, XP05584869, GB, ISSN: 1367-0484, DOI: 10.1016/j.clae.2003.11.002, abstract, table 1.

* cited by examiner

*Primary Examiner* — Carlos A Azpuru
(74) *Attorney, Agent, or Firm* — Sheng-Hsin Hu

(57) ABSTRACT

The present invention relates to a method to load a water insoluble phospholipid as nanoparticles to load into a hydrogel contact lens in autoclaving process during the hydrogel contact lens manufacturing process without an extra manufacturing step and without swelling the hydrogel contact lens with an organic solvent. The phospholipid nanoparticles loaded in hydrogel contact lens subsequently releases to the eye upon wearing.

13 Claims, No Drawings

CONTACT LENS PACKAGING SOLUTIONS

The present invention relates to a method to make a hydrogel contact loaded with phospholipid nanoparticles in autoclaving process during the hydrogel contact lens manufacturing process without an extra manufacturing step and without swelling the hydrogel contact lens with an organic solvent.

BACKGROUND OF THE INVENTION

Integrity of the tear film is essential for ocular surface homeostasis and functioning. Dry eye disease is a multifactorial condition characterized by tear film instability, and results in ocular discomfort and visual disturbance, severely impacting patient's quality of life. The outermost lipid layer of the tear film, formed by the meibum, helps to maintain tear film stability by reducing the rate of tear evaporation. Alteration in the tear lipid layer due to impaired quality or quantity of the meibum, is one of the most common cause of evaporative dry eye disease. Topically administered artificial tear substitutes/lubricant eye drops are the mainstay in the management of all types of dry eye disease and alleviate the symptoms and signs in patients with dry eye.

Chronic dry eye can lead to desiccation and damage of ocular surface tissues and disrupted epithelial cell barrier function. Instillation of lubricating artificial tears that replenish moisture and decrease friction is a primary approach to dry eye management.

However, one of the most, if not the most significant cause of discomfort, is the disruption of the protective lipid layer of the tear film over the ocular service resulting in subsequent desiccation of the ocular surface. Excessive evaporation also occurs from the front (anterior) surface of the contact lens.

Artificial tear compositions comprise compounds that lubricate and protect the ocular surface. In the context of dry eye disorders, artificial tear compositions can prevent symptoms such as pain and discomfort and can prevent bioadhesion and tissue damage induced by friction. For example, certain marketed artificial tear products contain a unique combination of ingredients that promotes the stability of small oil droplets within the emulsion. The emulsion also includes a mucoadhesive polymer that aid in delivering a lipid to the ocular surface. The lipid layer over the eye preserves the aqueous tear film. An evaporation barrier over the eye leading to an environment of increased humidity appears to enhance the tear film.

Though existing artificial tear compositions have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive, often leading to patient compliance issues.

There is still a need to develop longer-acting method to deliver lipid to the eyes that provide increased ocular hydration protection against desiccation and protection by surface retention for treating dry eye.

SUMMARY OF THE INVENTION

The present invention, in one aspect, a method for making a soft contact lens capable of releasing phosphatidylcholine nanoparticles comprising the steps of:

a) providing a phosphatidylcholine,
b) mixing the phosphatidylcholine with an aqueous solution having a pH of 1 to 4 to form a mixture, wherein the aqueous solution is free of an organic solvent.
c) high-energy treating the mixture of step b) to form a phosphatidylcholine nanoparticle in the mixture with a first concentration,
d) diluting the mixture of step c) with a buffered saline solution to form a packaging solution, wherein the packaging solution has phosphatidylcholiner nanoparticle with a second concentration, wherein the first concentration is higher than the second concentration,
e) packaging a hydrogel contact lens in a container containing the packaging solution,
f) autoclaving the hydrogel contact lens in the packaging solution to load the phosphatidylcholine nanoparticle into the hydrogel contact lens, wherein the packaging solution has a pH of from about 6.0 to 8.0, an osmolality of from about 200 to about 450 mOsm/kg, The present invention, in another aspect, provides an ophthalmic product, comprising a sealed and sterilized package which includes:

a packaging solution and a hydrogel contact lens immersed in the packaging solution, wherein the packaging solution includes,
a phosphatidylcholine nanoparticle, wherein the phosphatidylcholine nanoparticle is obtained by high-energy treating a mixture of an aqueous solution of the phosphatidylcholine, wherein the aqueous solution having a pH from 1 to 4 and is free of an organic solvent,
one or more buffering agents in an amount sufficient to provide the first aqueous solution a pH of from about 6.0 to 8.0,
one or more tonicity agents in an amount sufficient to provide the first aqueous solution an osmolality of from about 200 to about 450 mOsm/kg.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings.

"About" as used herein in this application means that a number, which is referred to as "about", comprises the recited number plus or minus 1-10% of that recited number.

A "hydrogel" or "hydrogel material" refers to a crosslinked polymeric material which has three-dimensional polymer networks (i.e., polymer matrix), is insoluble in water, but can hold at least 10% by weight of water in its polymer matrix when it is fully hydrated (or equilibrated).

A "silicone hydrogel" refers to a silicone-containing hydrogel obtained by copolymerization of a polymerizable composition comprising at least one silicone-containing monomer or at least one silicone-containing macromer or at least one crosslinkable silicone-containing prepolymer.

As used in this application, the term "non-silicone hydrogel" refers to a hydrogel that is theoretically free of silicon.

"Hydrophilic" as used herein, describes a material or portion thereof that will more readily associate with water than with lipids.

The term "room temperature" refers to a temperature of about 21° C. to about 27° C.

The term "soluble", in reference to a compound or material in a solvent, means that the compound or material can be dissolved in the solvent to give a solution with a concentration of at least about 0.5% by weight at room temperature.

The term "insoluble", in reference to a compound or material in a solvent, means that the compound or material can be dissolved in the solvent to give a solution with a concentration of less than 0.05% by weight at room temperature.

A "vinylic monomer" refers to a compound that has one sole ethylenically unsaturated group, is soluble in a solvent, and can be polymerized actinically or thermally.

As used in this application, the term "ethylenically unsaturated group" is employed herein in a broad sense and is intended to encompass any groups containing at least one >C=C< group. Exemplary ethylenically unsaturated groups include without limitation (meth)acryloyl

allyl, vinyl, styrenyl, or other C=C containing groups.

An "acrylic monomer" refers to a vinylic monomer having one sole (meth)acryloyl group. Examples of acrylic monomrs includes (meth)acryloxy [or(meth)acryloyloxy] monomers and (meth)acrylamido monomers.

An "(meth)acryloxy monomer" or "(meth)acryloyloxy monomer" refers to a vinylic monomer having one sole group of

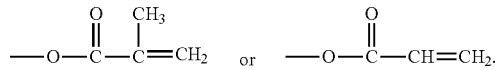

An "(meth)acrylamido monomer" refers to a vinylic monomer having one sole group of

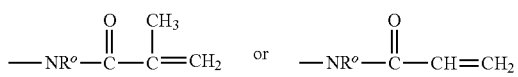

in which $R^o$ is H or $C_1$-$C_4$ alkyl.

The term "(meth)acrylamide" refers to methacrylamide and/or acrylamide.

The term "(meth)acrylate" refers to methacrylate and/or acrylate.

An "N-vinyl amide monomer" refers to an amide compound having a vinyl group (—CH=CH$_2$) that is directly attached to the nitrogen atom of the amide group.

The term "terminal (meth)acryloyl group" refers to one (meth)acryloyl group at one of the two ends of the main chain (or backbone) of an organic compound as known to a person skilled in the art.

As used herein, "actinically" in reference to curing, crosslinking or polymerizing of a polymerizable composition, a prepolymer or a material means that the curing (e.g., crosslinked and/or polymerized) is performed by actinic irradiation, such as, for example, UV/visible irradiation, ionizing radiation (e.g. gamma ray or X-ray irradiation), microwave irradiation, and the like. Thermal curing or actinic curing methods are well-known to a person skilled in the art.

A "hydrophilic vinylic monomer", a "hydrophilic acrylic monomer", a "hydrophilic (meth)acryloxy monomer", or a "hydrophilic (meth)acrylamido monomer", as used herein, respectively refers to a vinylic monomer, an acrylic monomer, a (meth)acryloxy monomer, or a (meth)acrylamido monomer), which typically yields a homopolymer that is water-soluble or can absorb at least 10 percent by weight of water.

A "hydrophobic vinylic monomer", a "hydrophobic acrylic monomer", a "hydrophobic (meth)acryloxy monomer", or a "hydrophobic (meth)acrylamido monomer", as used herein, respectively refers to a vinylic monomer, an acrylic monomer, a (meth)acryloxy monomer, or a (meth)acrylamido monomer), which typically yields a homopolymer that is insoluble in water and can absorb less than 10% by weight of water.

As used in this application, the term "vinylic crosslinker" refers to an organic compound having at least two ethylenically unsaturated groups. A "vinylic crosslinking agent" refers to a vinylic crosslinker having a molecular weight of 700 Daltons or less.

As used in this application, the term "polymer" means a material formed by polymerizing/crosslinking one or more monomers or macromers or prepolymers or combinations thereof.

As used in this application, the term "molecular weight" of a polymeric material (including monomeric or macromeric materials) refers to the number average molecular weight unless otherwise specifically noted or unless testing conditions indicate otherwise.

A "polysiloxane segment" refers to a polymer chain consisting of at least three consecutively- and directly-linked siloxane units (divalent radical) each independent of one another having a formula of

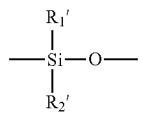

in which $R_1'$ and $R_2'$ are two substituents independently selected from the group consisting of $C_1$-$C_{10}$ alkyl, $C_1$-$C_4$-alkyl- or $C_1$-$C_4$-alkoxy-substituted phenyl, $C_1$-$C_{10}$ fluoroalkyl, $C_1$-$C_{10}$ fluoroether, $C_6$-$C_{18}$ aryl radical, -alk-(OC$_2$H$_4$)$_{\gamma 1}$-OR$^o$ (in which alk is $C_1$-$C_6$ alkyl diradical, $R^o$ is H or $C_1$-$C_4$ alkyl and $\gamma 1$ is an integer from 1 to 10), a $C_2$-$C_{40}$ organic radical having at least one functional group selected from the group consisting of hydroxyl group (—OH), carboxyl group (—COOH), —NR$_3$'R$_4$', amino linkages of —NR$_3$'—, amide linkages of —CONR$_3$'—, amide of —CONR$_3$'R$_4$', urethane linkages of —OCONH—, and C$_1$-C$_4$ alkoxy group, or a linear hydrophilic polymer chain, in which R$_3$' and R$_4$' independent of each other are hydrogen or a C$_1$-C$_{15}$ alkyl.

A "polysiloxane vinylic crosslinker" refers to a compound comprising at least one polysiloxane segment and at least two ethylenically-unsaturated groups.

A "linear polysiloxane vinylic crosslinker" refers to a compound comprising a main chain which includes at least one polysiloxane segment and is terminated with one ethylenically-unsaturated group at each of the two ends of the main chain.

A "chain-extended polysiloxane vinylic crosslinker" refers to a compound comprising at least two ethylenically-unsaturated groups and at least two polysiloxane segments each pair of which is linked by one divalent radical.

The term "fluid" as used herein indicates that a material is capable of flowing like a liquid.

The term "room temperature" refers to a temperature of about 21° C. to about 27° C.

As used in this application, the term "clear" in reference to a polymerizable composition means that the polymerizable composition is a transparent solution or liquid mixture (i.e., having a light transmissibility of 85% or greater, preferably 90% or greater in the range between 400 to 700 nm).

In accordance with the invention, a packaging solution is ophthalmic safe. The term "ophthalmically safe" with respect to a packaging solution is meant that a contact lens immersed in the solution is safe for direct placement on the eye without rinsing, that is, the solution is safe and sufficiently comfortable for daily contact with the eye via a contact lens. An ophthalmically safe solution has a tonicity and pH that is compatible with the eye and comprises materials, and amounts thereof, that are non-cytotoxic according to international ISO standards and U.S. FDA regulations.

The term "high-energy treating of the mixture Phosphatidylcholines (PC) and an aqueous solution having a pH of 1 to 4" means that subjecting the mixture of Phosphatidylcholines (PC) and an aqueous solution having a pH of 1 to 4 with a high speed stirring, a high pressure homogenizer or sonicating without using any solvent except of water. The high-energy treating is carried out at room temperature at least initially and without adding heat except of the heat is generated by the treating itself.

The term "a high speed stirring" means that subjecting the mixture under at least 800 rpm stirring, or preferred at least 1000 rpm.

The term "sonicating" means that subjecting the mixture under applying sound energy. In the laboratory, it is usually applied using an ultrasonic bath or an ultrasonic probe, colloquially known as a sonicator. Ultrasonic frequencies (>20 kHz) are usually used, leading to the process also being known as ultrasonication or ultra-sonication.

The term "a high pressure homogenizing" means that subjecting the mixture of two mutually non-soluble liquids the same throughout. This is achieved by turning one of the liquids into a state consisting of extremely small particles distributed uniformly throughout the other liquid. A typical example is the homogenization of milk, where the milk fat globules are reduced in size and dispersed uniformly through the rest of the milk. For example, milk homogenization is accomplished by mixing large amounts of harvested milk, then forcing the milk at high pressure through small holes.

Saline solution is a mixture of salt and water. Normal saline solution contains 0.9 percent sodium chloride (salt), which is similar to the sodium concentration in blood and tears.

Saline has many uses in medicine. It's used to clean wounds, clear sinuses, and treat dehydration. Normal saline is a mixture of salt and water. It is called normal because its salt concentration is similar to tears, blood and other body fluids (0.9% saline). It is also called isotonic solution.

"Buffered saline" means normal saline in various buffer, for example, PBS refers to 0.9% NaCl solution in Phosphate buffer. Phosphate-buffered saline (abbreviated PBS) is a buffer solution commonly used in biological research. It is a water-based salt solution containing disodium hydrogen phosphate, sodium chloride and, in some formulations, potassium chloride and potassium dihydrogen phosphate. The buffer helps to maintain a constant pH.

Tris is short for tris(hydroxymethyl) aminomethane, a chemical compound which is often used in saline because it is isotonic and non-toxic. Tris-buffered saline (TBS) is a buffer used in some biochemical techniques to maintain the pH within a relatively narrow range. Tris (with HCl) has a slightly alkaline buffering capacity in the 7-9.2 range. The conjugate acid of Tris has a pKa of 8.07 at 25 ° C. The pKa declines approximately 0.03 units per degree Celsius rise in temperature. This can lead to relatively dramatic pH shifts when there are shifts in solution temperature. Sodium chloride concentration may vary from 100 to 200 mM, tris concentration from 5 to 100 mM and pH from 7.2 to 8.0. A common formulation of TBS is 150 mM NaCl, 50 mM Tris-HCl, pH 7.6. TBS can also be prepared by using commercially made TBS buffer tablets or pouches.

A "phosphatidylcholine nanoparticle" refers to particles which is made of one or more phosphatidylcholine material and have a size (radius) of less than 100 nm but higher than 5 nm, preferred less than 50 nm but higher than 5 nm, more preferred less than 30 nm but higher than 5 nm.

A "leachable phosphatidylcholine nanoparticles" as used herein refer to a phosphatidylcholine nanoparticles which is not covalently bound to but instead is associated with or entrapped within the polymer matrix of a contact lens and which releases out the phosphatidylcholine nanoparticles from the hydrogel contact lens to the eye upon wearing.

The term "an aqueous solution" refers to a solution in which the only solvent is water.

The present invention is generally directed to a method for making a soft contact lens capable of releasing phosphatidylcholine nanoparticles comprising the steps of:
  a) providing a phosphatidylcholine,
  b) mixing the phosphatidylcholine with an aqueous solution having a pH of 1 to 4 to form a mixture, wherein the aqueous solution is free of an organic solvent,
  c) high-energy treating the mixture of step b) to form a phosphatidylcholine nanoparticle in the mixture with a first concentration,
  d) diluting the mixture of step c) with a buffered saline solution to form a packaging solution, wherein the packaging solution has phosphatidylcholiner nanoparticle with a second concentration, wherein the first concentration is higher than the second concentration,
  e) packaging a hydrogel contact lens in a container containing the packaging solution,
  f) autoclaving the hydrogel contact lens in the packaging solution to load the phosphatidylcholine nanoparticle into the hydrogel contact lens, wherein the packaging solution has a pH of from about 6.0 to 8.0, an osmolality of from about 200 to about 450 mOsm/kg, The present invention is partly based on the discovery that phosphatidylcholine nanoparticles can be formed in an aqueous solution free of an organic solvent by high energy treating the mixture of water insoluble phosphatidylcholine and an aqueous solution having a pH from 1 to 4. The present invention is also partly based on the discovery that at pH lower than pKa, the negative charge of phosphate group in phosphatidylcholine is neutralized through the protonation, which break static stacking in phosphatidylcholine crystal and improve solubility of phosphatidylcholine in an aqueous solution (scheme 1). For example, according to the experimental results of the present application, DMPC is dissolved (pKa 1.86) into 137 mM of HCl aqueous solution up to 10 mg/mL and induced aggregate and formed nanoparticles (~30 nm) by stirring at room temperature for about 10 hours. After neutralized by NaOH, the nanoparticles were diluted to certain concentration in packing saline.

The present invention is also partly based on the discovery that phosphatidylcholine nanoparticles can be loaded into a hydrogel contact lens by immersing hydrogel contact lens into the phosphatidylcholine nanoparticles containing packaging solution before typical autoclaving process in the manufacturing hydrogel contact lens without an extra manufacturing step and without swelling the hydrogel contact lens with an organic solvent. For example, according to the experimental results of the present application, DMPC was loaded into contact lens (25-65 ug/lens) during autoclave in above packing saline with DMPC nanoparticles (0.1-1 mg/mL).

In accordance with the invention, a soft hydrogel contact lens can be a conventional hydrogel contact lens (i.e., a non-silicone hydrogel lens) or preferably a silicone hydrogel contact lens.

Any phosphatidylcholines (PC) can be used in this invention. Phosphatidylcholines are a class of phospholipids that incorporate choline as a headgroup. They are a major component of biological membranes and can be easily obtained from a variety of readily available sources, such as egg yolk or soybeans, from which they are mechanically or chemically extracted using hexane. Purified phosphatidylcholine is produced commercially.

Examples of Phosphatidylcholine includes without limitation, Phosphatidylcholine includes 1,2-Didecanoyl-sn-glycero-3-phosphocholine (DDPC), 1,2-Dilauroyl-sn-glycero-3-phosphorylcholine (DLPC), Dimyristoylphosphatidylcholine (DMPC), Dipalmitoylphosphatidylcholine (DPPC), 1,2-Distearoyl-sn-glycero-3-phosphocholine (DSPC), 1,2-Dioleoyl-sn-Glycero-3-Phosphocholine (DOPC), 1-palmitoyl-2-oleoyl-sn-glycero-3-phosphocholine (POPC), 1,2-Dierucoyl-sn-Glycero-3-Phosphatidylcholine (DEPC), dihexanoyl phosphatidylcholine(DHPC). Such preferred Phosphatidylcholine are commercially available, such as NOF Corporationj, Echelon Biosciences, sigma-Aldrich. In accordance with the invention, the preferred Phosphatidylcholine is Dimyristoylphosphatidylcholine (DMPC).

According to the present application, in the prepare phosphatidylcholine nanoparticles, the phosphatidylcholine is typically at least 0.01 w/v %, more typically at least 0.05 w/v % and even more typically at least 0.1 w/v % of the mixture of phosphatidylcholineans and an aqueous solution having a Scheme 1 of DMPC structure at pH 7 (left) and pH 1 (right).

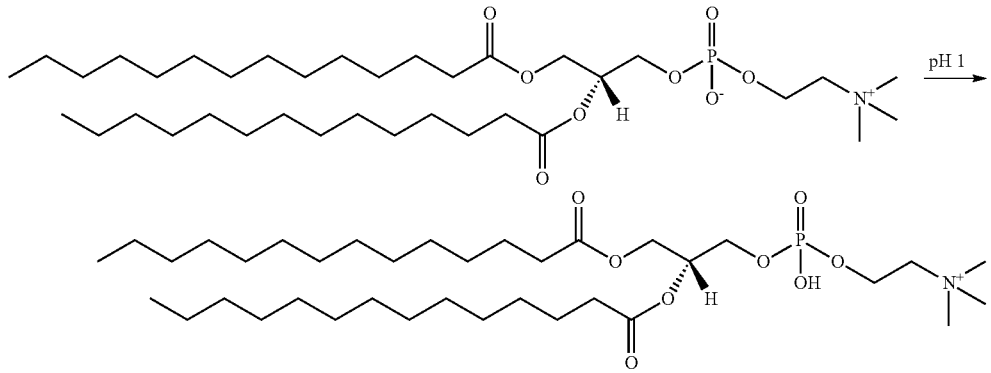

The present invention is further partly based on the discovery that the phosphatidylcholine nanoparticles loaded hydrogel contact lens can release phosphatidylcholine nanoparticles to the eye upon wearing.

Lens packages (or containers) are well known to a person skilled in the art for autoclaving and storing a soft contact lens. Any lens packages can be used in the invention. Preferably, a lens package is a blister package which comprises a base and a cover, wherein the cover is detachably sealed to the base, wherein the base includes a cavity for receiving a sterile packaging solution and the contact lens.

Lenses are packaged in individual packages, sealed, and sterilized (e.g., by autoclave at about 120° C. or higher for at least 30 minutes) prior to dispensing to users. A person skilled in the art will understand well how to seal and sterilize lens packages.

pH from 1 to 4. The phosphatidylcholine is also typically no greater than about 10 w/v %, more typically no greater than about 5 w/v % and even more typically no greater than about 3 or even 1.5 w/v % of the aqueous solution having a pH from 1 to 4. In the prepare phosphatidylcholine nanoparticles, examples of preferred pH is from 1 to 4, more preferred from 1 to 3, still more preferred from 1 to 2.

According to the present application, high-energy treating the mixture Phosphatidylcholines (PC) and an aqueous solution having a pH from 1 to 4 with a high speed stirring, a high pressure homogenizer or sonicating without using any solvent except of water.

For example, a high speed stirring treating is subjecting the mixture under at least 800 rpm stirring, or preferred at least 1000 rpm for an amount of time such as 24 hours.

Sonicating treating is subjecting the mixture in a sonicator (60 Hz, water batch) for an amount of time such as 2 hours.

According to the present application, high-energy treating the mixture of phosphatidylcholine and an aqueous solution having a pH from 1 to 4 to form a phosphatidylcholiner nanoparticle with a first concentration in the mixture. The aqueous solution is water, de-ionized water or a buffered saline solution and is free of organic solvent. Then, diluting the mixture of phosphatidylcholiner nanoparticles an aqueous solution having a pH from 1 to 4 with a buffered saline solution to form a packaging solution with a lower concentration of phosphatidylcholiner nanoparticles than the first concentration. The packaging solution has a pH of from about 6.0 to about 8.0, an osmolality of from about 200 to about 450 mOsm/kg. The pH of the packaging solution is measured after the dilution and adjusted, if necessary, to the targeted value of from about 6.0 to about 8.0. A personal skilled in the art would know how to adjust pH by adding NaOH or HCL.

The diluting the mixture with a buffered saline solution is at a ratio of 1:1000 to 1:10, preferred 1:500 to 1:15, more preferred 1:300 to 1:20, even more preferred 1:150 to 1:30 depending on the initial phosphatidylcholiner nanoparticles concentration.

The phosphatidylcholiner nanoparticles concentration in the packaging solution for packaging the hydrogel contact lens is from 25 ppm to 3000 ppm, preferred from 50 ppm to 2500 ppm, more preferred from 100 ppm to 2000 ppm.

According to the present application, any kind of hydrogel contact lenses can be loaded with phosphatidylcholine nanoparticles by autoclaving the hydrogel contact lens in the phosphatidylcholiner nanoparticle containing packaging solution. The preferred hydrogel contact lens is a silicone hydrogel contact lens. According to the present application, through autoclaving loading process, hydrogel contact lenses are loaded with phosphatidylcholine nanoparticles from 10 μg/lens to 100 μg/lens, preferred from 15 μg/lens to 90 μg/lens, more preferred from 20 μg/lens to 80 μg/lens .

The packaging solution of the present invention preferably contains a buffering agent. The buffering agents maintain the pH preferably in the desired range, for example, in a physiologically acceptable range of about 6 to about 8. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (2-amino-2-hydroxymethyl-1,3-propanediol), Bis-Tris (Bis-(2-hydroxyethyl)-imino-tris-(hydroxymethyl)-methane), bis-aminopolyols, triethanolamine, ACES (N-(2-hydroxyethyl)-2-aminoethanesulfonic acid), BES (N,N-Bis (2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N, N'-bis(2-ethanesulfonic acid), TES (N-[Tris(hydroxymethyl)methyl]-2-aminoethanesulfonic acid), salts thereof, phosphate buffers, e.g. $Na_2HPO_4$, $NaH_2PO_4$, and $KH_2PO_4$ or mixtures thereof. A preferred bis-aminopolyol is 1,3-bis (tris[hydroxymethyl]-methylamino)propane (bis-TRIS-propane). The amount of each buffer agent is that amount necessary to be effective in achieving a pH of the composition of from about 6.5 to about 7.5. Typically, it is present in an amount of from 0.001% to 2%, preferably from 0.01% to 1%; most preferably from about 0.05% to about 0.30% by weight.

The packaging solutions according to the invention are preferably formulated in such a way that they are isotonic with the lachrymal fluid. A solution which is isotonic with the lachrymal fluid is generally understood to be a solution whose concentration corresponds to the concentration of a 0.9% sodium chloride solution (308 mOsm/kg). Deviations from this concentration are possible throughout.

The isotonicity with the lachrymal fluid, or even another desired tonicity, may be adjusted by adding organic or inorganic substances which affect the tonicity. Suitable occularly acceptable tonicity agents include, but are not limited to sodium chloride, potassium chloride, glycerol, propylene glycol, polyols, mannitols, sorbitol, xylitol and mixtures thereof. Preferably, the majority of the tonicity of the solution is provided by one or more compounds selected from the group consisting of non-halide containing electrolytes (e.g., sodium bicarbonate) and non-electrolytic compounds. The tonicity of the solution is typically adjusted to be in the range from about 200 to about 450 milliosmol (mOsm), preferably from about 250 to 350 mOsm.

A packaging solution of the invention can optionally include a viscosity-enhancing polymers, which can be a water soluble cellulose-derived polymer, a water-soluble polyvinylalcohol (PVA), or combination thereof. Examples of useful cellulose-derived polymers include without limitation cellulose ethers. Exemplary preferred cellulose ethers are methyl cellulose (MC), ethyl cellulose, hydroxymethylcellulose, hydroxyethyl cellulose (HEC), hydroxypropylcellulose (HPC), hydroxypropylmethyl cellulose (HPMC), or a mixture thereof. More preferably, a cellulose ether is hydroxyethyl cellulose (HEC), hydroxypropylmethyl cellulose (HPMC), and mixtures thereof. The cellulose ether is present in the composition in an amount of preferably from about 0.1% to about 1% by weight, based on the total amount of the packaging solution.

In accordance with the invention, the packaging solution can further comprises mucin-like materials, ophthalmically beneficial materials, and polymers.

Exemplary mucin-like materials include without limitation polyglycolic acid and polylactides. A mucin-like material can be used as guest materials which can be released continuously and slowly over extended period of time to the ocular surface of the eye for treating dry eye syndrome. The mucin-like material preferably is present in effective amounts.

Exemplary ophthalmically beneficial materials include without limitation 2-pyrrolidone-5-carboxylic acid (PCA), amino acids (e.g., taurine, glycine, etc.), alpha hydroxyl acids (e.g., glycolic, lactic, malic, tartaric, mandelic and citric acids and salts thereof, etc.), linoleic and gamma linoleic acids, and vitamins (e.g., B5, A, B6, etc.).

Exemplary polymers include without limitation polyamine-epichlorohydrin or polyamidoamine-epichlorohydrin (PAE) and polyacrylamide-poly(acrylic acid) (PAAm-PAA) copolymer which form in packaging coating (IPC) onto contact lens surface to improve its surface properties such as lubricity as described in U.S. Pat. No. 9,575,332 B2.

A lens can be prepared according to any methods known to a person skilled in the art from a hydrogel lens-forming formulation. A "hydrogel lens-forming formulation" or "hydrogel lens-forming material" refers to a polymerizable composition which can be cured (i.e., polymerized and/or crosslinked) thermally or actinically to obtain a crosslinked/polymerized polymeric material. Lens-forming materials are well known to a person skilled in the art. Typically a lens forming material comprises polymerizable/crosslinkable components, for example, such as, monomers, macromers, prepolymers, or combinations thereof, as known to a person skilled in the art. A lens-forming material can further include other components, such as non-crosslinkable hydrophilic polymers (i.e., leachable polymeric lubricants), an initiator (e.g., a photoinitiator or a thermal initiator), a visibility tinting agent, UV-blocking agent, photosensitizers, antimicrobial agents (e.g., Ag-nanoparticles), and the like.

Examples of lens making include without limitation, cast-molding, spin-casting, and lathing. A person skilled in the art will know well how to cast-mold lenses from a lens-forming formulation in molds based on thermal or actinic polymerization.

In accordance with the present invention, a hydrogel lens-forming formulation (or a polymerizable fluid composition) can be a solution or a solvent-free liquid or melt at a temperature below 60° C.

The present invention, in another aspect, provides an ophthalmic product, comprising a sealed and sterilized package which includes:
  a packaging solution and a hydrogel contact lens immersed in the packaging solution, wherein the packaging solution includes,
  a phosphatidylcholine nanoparticle, wherein the phosphatidylcholine nanoparticle is obtained by high-energy treating a mixture of an aqueous solution of the phosphatidylcholine, wherein the aqueous solution having a pH from 1 to 3 and is free of an organic solvent,
  one or more buffering agents in an amount sufficient to provide the first aqueous solution a pH of from about 6.0 to 8.0,
  one or more tonicity agents in an amount sufficient to provide the first aqueous solution an osmolality of from about 200 to about 450 mOsm/kg.

Above described various embodiments and preferred embodiments of packaging solutions, hydrogel lens-forming formulations (lens-forming materials), leachable lubricants, packages, sealing and sterilization, and the others can be used in this aspect of the invention.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

EXAMPLE 1

Lens Packaging Solutions Containing Dimyristoylphosphatidylcholine (DMPC) Nanoparticles Method: DMPC was added into 135 mM of HCl and stirred overnight at room temperature to form nanoparticles (4-440 mg/mL). Then, pH was adjusted to 6-8 by 50% NaOH. The solution was diluted by PBS or Saline 14 to get certain concentration (0.1-2 mg/mL).

Loading: After extraction (IPA, PAA) and rinse steps, DT1-thermal lens was packed in 0.65 mL/lens of saline with DMPC, then, autoclaved at 120° C. for 45 min.

Loading Test: At least 1 day after autoclave, lens was rinse in DI water (5 mL per lens) for 10 min and extract by nPA (1 ml/lens) for 24 h. Extracted DMPC amount was determined by HPLC method.

Particles size (diameter or radius) value in the packaging formulation of DMPC was determined by NanoStar which configured with a 90° scattering angle and an 830 nm solid state diode laser. The instrument simultaneously providing total scattering intensity and hydrodynamic radius which enables to study particles size of range up to 2500 nm and system homogeneity of the packaging formulation. It is easy to use without perturbation of the formulation for detecting particles size containing DMPC. The instrument temperature was set at 25° C. All measurements were made using a 45 µl quartz cuvette sample cell to maximum the output of signals without filtering the sample. Carefully pipet 100 µl formulation into quartz cuvette using micropipette to avoid forming air bobbles in the cuvette for accurate data. The outside quartz cuvette then cleaned with Kimwise paper and placed in the measurement compartment for measurement. 30 scans were taken to get average of particles size. The run time is 10 minutes. Data were analysed by Wyatt DynaPro software.

Example of Lens Process

EXAMPLE 2

Preparation of CE-PDMS Macromer

In the first step, .alpha.,.omega.-bis(2-hydroxyethoxypropyl)-polydimethylsiloxane (Mn=2000, Shin-Etsu, KF-6001a) is capped with isophorone diisocyanate (IPDI) by reacting 49.85 g of .alpha.,.omega.-bis(2-hydroxyethoxypropyl)-polydimethylsiloxane with 11.1 g IPDI in 150 g of dry methyl ethyl ketone (MEK) in the presence of 0.063 g of dibutyltindilaurate (DBTDL). The reaction is kept for 4.5 h at 40.degree. C., forming IPDI-PDMS-IPDI. In the second step, a mixture of 164.8 g of .alpha.,.omega.-bis(2-hydroxyethoxypropyl)-polydimethylsiloxane (Mn=3000, Shin-Etsu, KF-6002) and 50 g of dry MEK are added dropwise to the IPDI-PDMS-IPDI solution to which has been added an additional 0.063 g of DBTDL. The reactor is held for 4.5 h at about 40.degree. C., forming HO-PDMS-IPDI-PDMS-IPDI-PDMS-OH. MEK is then removed under reduced pressure. In the third step, the terminal hydroxyl-groups are capped with methacryloyloxyethyl groups in a third step by addition of 7.77 g of isocyanatoethylmethacrylate (IEM) and an additional 0.063 g of DBTDL, forming IEM-PDMS-IPDI-PDMS-IPDI-PDMS-IEM (CE-PDMS macromer).

Alternate Preparation of CE-PDMS Macromer 240.43 g of KF-6001 is added into a 1-L reactor equipped with stirring, thermometer, cryostat, dropping funnel, and nitrogen/vacuum inlet adapter, and then dried by application of high vacuum (2.times.10.sup.-2 mBar). Then, under an atmosphere of dry nitrogen, 320 g of distilled MEK is then added into the reactor and the mixture is stirred thoroughly. 0.235 g of DBTDL is added to the reactor. After the reactor is warmed to 45.degree. C., 45.86 g of IPDI are added through an addition funnel over 10 minutes to the reactor under moderate stirring. The reaction is kept for 2 hours at 60.degree. C. 630 g of KF-6002 dissolved in 452 g of distilled MEK are then added and stirred until a homogeneous solution is formed. 0.235 g of DBTDL are added, and the reactor is held at about 55.degree. C. overnight under a blanket of dry nitrogen. The next day, MEK is removed by flash distillation. The reactor is cooled and 22.7 g of IEM are then charged to the reactor followed by about 0.235 g of DBTDL. After about 3 hours, an additional 3.3 g of IEM are added and the reaction is allowed to proceed overnight. The following day, the reaction mixture is cooled to about 18.degree. C. to obtain CE-PDMS macromer with terminal methacrylate groups.

EXAMPLE 3

Preparation of Polymerizable Compositions

All polymerizable compositions (i.e., "formulations") are prepared at room temperature in air by blending all the components listed in Table 1 besides Vazo-64 for 30-120 minutes using a magnetic stir plate. Then above mixture is cooled down in ice bath for 10 min, added thermal initiator Vazo-64 (2,2'-dimethyl-2,2'azodipropionitrile) and blended for 30 min. CE-PDMS (Mn 12.0 KD) represents a polysiloxane vinylic crosslinker which has three polydimethylsiloxane (PDMS) segments linked via diurethane linkages between two PDMS segments and two urethane linkages each located between one terminal methacrylate group and one PDMS segment and is prepared according to example above for Example 2 (Preparation of CE-PDMS Macromer). TrisAm represents (N-[tris(trimethylsiloxy)-silylpropyl]acrylamide); DMA represents N,N-dimethylacrylamide, Vazo-64 represents 2,2'-dimethyl-2,2'azodipropionitrile; Nobloc is 2-[3-(2H-Benzotriazol-2-yl)-4-hydroxyphenyl]ethyl methacrylate from Aldrich; RB247 is Reactive Blue 247; UV28 represents 2-{2'-Hydroxy-3'-tert-butyl-5'-[3'-methacryloyloxypropoxy]phenyl}-5-chloro-2H-benzotriazole; PrOH represents n-propanol.

TABLE 1

| Formulation | DTCO1 |
|---|---|
| PrOH | 5 |
| DMA | 32 |
| NORBLOC | 1.50 |
| UV28 | 0.40 |
| RB247 | 0.01 |
| TRIS-Am | 28 |
| CE-PDMS | 40 |
| Vazo-64 | 0.50 |
| TOTAL = | 108.41 |

EXAMPLE 4

Cast Molding Including Curing and Post-Curing Treatment

A lens formulation is purged with nitrogen at room temperature for 30 to 35 minutes. The $N_2$-purged lens formulation is introduced into polypropylene molds and the molds are closed and placed in an oven. The oven is configured as follows: a nitrogen supply is connected to the oven through a higher flow capacity controller whichcan control the flow rate of nitrogen through the oven; at the exhaust line of the oven, vacuum pumps are connected to control the differential pressure of the oven.

The polymerizable compositions in the molds are thermally cured in the oven under the following conditions: (1) purging the oven for about 30 minutes by flowing nitrogen through the oven at a flow rate (e.g., 60 cubic foot per hour); (2) ramping from room temperature to a first curing temperature (e.g., 55° C.) and then holding at the first curing temperature for a first curing time period (about 40 minutes) while keeping nitrogen flow at a flow rate (e.g., 40 cubic foot per hour); (3) ramping from the first curing temperature to a second curing temperature (e.g., 80° C.) and holding at the second curing temperature for a second curing time period (e.g., about 40 minutes) while keeping nitrogen flow at a flow rate (e.g., about 40 cubic foot per hour); (4) ramping from the second curing temperature to a third curing temperature (e.g., 100° C.) and holding at the third curing temperature for a third curing time period (e.g., about 40 minutes) while keeping nitrogen flow at the $2^{nd}$ flow rate; and (6) cooling from the post-curing temperature to room temperature before opening the oven and removing the molds from the oven.

EXAMPLE 5

Mold Separation

Lens molds each with a molded silicone hydrogel contact lens precursor therein are mechanically opened. The molded unprocessed silicone hydrogel contact lens precursors adhere to the male mold halves.

Removing Lens Precursors from Lens-Adhered Mold Halves

Molded unprocessed silicone hydrogel contact lenses are removed (i.e., "delensed") from lens-adhered male mold halves by using an ultrasonic welding apparatus. The ultrasonic vibration energy used in delensing is about 8 J. The trigger force is about 100 N.

EXAMPLE 6

Wet Process

Dry lens delensed from above step was soaking in pure PrOH solution for 3 h, 0.44% PAA/PrOH solution for 30 min, 50/50 v/v PrOH/H2O for 20 min, then rinse with 25 mM PB solution for 15 min twice.

DMPC Loading: After wet process (extraction and PAA coating), DT1 thermal lenses are packed into DMPC nanoparticles packaging solution in hybrid shell and autoclaved at 121° C. for 45 min. To measure loading amount of DMPC, lens is unpacked, rinse in DI water for 5 seconds, and extracted in 2 mL of methanol for 24 h.

An UPLC with ELSD detector that used in the present invention is to provide method to carry out the assay method of DMPC from lenses extraction. Method of the present UPLC with ELSD detector shows the separation method from the following steps:

(1) chromatographic condition: Waters UPLC system with detecting device ELSD detector, lmtakt Scherzo SM-C18 Column, 2 mm×150 mm, or equivalent was successful develop a reproducible and reliable chromatographic analysis with excellent peak shape; The mobile phase of chromatographic condition is made up of 0.5M Ammonium Formate in Water (mobile phase A)—Wherein Methanol (mobile phase B). The mobile phase was filtered on 0.45 μm nylon filter. Gradient scheme were start at 10% A/90% B for RT 10 min then decreased to 8% A/92% B this ratio for 6 minutes (at RT 16 min). The gradient ratio returned to 10% A/190% B at RT 17 min. The flow rate is 0.5 mL per minutes. Column temperature was set at 60° C. with run time 25 minutes.

(2) preparation of reference standards: follow the example to prepare proper amount of DMPC and prepare by adding the substances into the methanol for series of reference standards of which every 1 ml contains 10 μg to 50 μg of DMPC, and use the solution as a reference standards;

(3) preparation of extracted lens solution (1 lens/per ml in methanol) of which every 1 ml methanol contains about 1 lens in 2 mL glass vial, then slowly shaking overnight at room temperature before HPLC run.

(4) assay method: careful removed extracted lens solution to HPLC vial by glass pipet. Inject 50 μl into liquid chromatography and check detection sensitivity. The major DMPC chromatogram peak height is about 50% of full scale, get several injections for optimum chromatography, record chromatogram to method. The retention time for DMPC in the chromatogram is about 16 minutes. Total time of assay is less than 25 minutes. Repeat 5 times of DPMC peak retention time and the peak area for system suitability before run.

The present HPLC assay method for DMPC detection limit. Diluted to the solution of a series of variable concentrations with methanol, respectively. Inject 50 µl sample, make it to produce the signal that DMPC peak is 3 times of baseline noise. Through test, detectability is 1 µg/mL (S/N>=3), if calculate with concentration 30 mg/ml during DMPC separation, its limit of detection is 2 ug/mL.

The HPLC assay method for DMPC linearity curve by the preparation of reference standards in methanol, dissolves and be diluted to scale. The concentration range is in 10~50 µg/ml, peak area and concentration are good linear relationship, and its range of linear square regression coefficient is 0.99

The HPLC assay method of DMPC extracted from Lens, be applicable to variously need the method for carrying out related preparations of Lens preparation, as of Lens packaging solution, and any lenses composition contains DMPC.

The present method good effects:

1. the present invention uses ELSD detection to carry out DMPC from lenses extract by evaluation chromatographic peak retention time and peak area. The DMPC released from lenses extract that can be calculated from chromatographic peak area and identify by the position of retention time. The ELSD spectra information that can provide qualitative, and qualitatively and effectively detection sensitivity.
2. the present UPLC assay method separated DMPC from other lenses substance which can rapidly and accurately control product quality preferably.
3. the assay method for the present invention is applicable to various lenses formulation and its related packaging solution preparations.
4. the present HPLC assay method is accurate, simple to operate, and favorable reproducibility is highly sensitive, fully meet the requirement in Quality control, guarantee product quality at work.

EXAMPLE 7

Preparing: DMPC was added into 135 mM of HCl and stirred overnight at RT to form nanoparticles (4 mg/mL). Then, pH was adjusted to 6-8 by 50% NaOH. The solution was diluted by PBS or Saline 14 to get certain concentration (0.1-2 mg/mL).

Loading: After extraction (IPA, PAA) and rinse steps, DT1-thermal lens was packed in 0.65 mL/lens of saline with DMPC, then, autoclaved at 120oC for 45 min.

Loading Test: At least 1 day after autoclave, lens was rinse in DI water (5 mL per lens) for 10 min and extract by nPA (1 ml/lens) for 24 h. Extracted DMPC amount was determined by HPLC method.

Releasing test: At least 1 day after autoclave, lens was soaked in artificial tear fluid (ATF) at 37 oC for a certain time. Concentration of DMPC in ATF was determined by HPLC method.

The DMPC loading results with diluting by PBS (control Saline) or Saline 14 are shown in the Table 2.

TABLE 2

DMPC loading results

| LOT # | Solution | Loading µg/lens |
|---|---|---|
| A | 1 mg/mL DMPC in control Saline (no IPC) | 57 |
| B | 2 mg/mL DMPC in Saline 14 | 69 |
| C | 1 mg/mL DMPC in Saline 14 | 67 |
| D | 0.5 mg/mL DMPC in Saline 14 | 55 |
| E | 0.2 mg/mL DMPC in Saline 14 | 44 |
| F | 0.1 mg/mL DMPC in Saline 14 | 25 |

The table data indicates that the higher DMPC concentration in the packaging solution, the higher DMPC loading in the contact lens. However the increase in DMPC loading in the contact lens is not proportional to the increase in the DMPC concentration in the packaging solution. For example, increase in the DMPC concentration in the packaging solution from 0.1 mg/ml to 0.5 mg/ml only results in the increase in DMPC loading in the contact lens from 25 µg/lens to 55 mg/ml.

Particles size in the packaging formulation of DMPC was determined by NanoStar as described before. Particle sizes of DMPC nanoparticles are diameter around 20-30 nm in both PBS and saline 14.

PBS (control Saline) composition is shown in the Table 3 and Saline 14 solution composition is shown in Table 4.

TABLE 3

PBS (control Saline) composition

| | |
|---|---|
| $NaH_2PO_4 \cdot H_2O$ | 0.044% (w/w) ± 0.5% of nominal |
| $Na_2HPO_4 \cdot 2H_2O$ | 0.388% (w/w) ± 0.5% of nominal |
| NaCl | 0.79% (w/w) ± 0.5% of nominal |
| NaOH or HCl | To achieve target pH |
| Hydrogen peroxide | 6 ± 1 ppm (peroxide added after heat pretreatment) |
| DI water | q.s. to 100% to account for differences in the PAE target. |
| Initial pH (prior to pre-reaction) and final pH | 7.4 ± 0.2 |

TABLE 4

Saline 14 solution composition
Saline 14 solution

| | |
|---|---|
| PAE concentration | Target wt% = [batch size * (0.05/NMR)]/(% solids) |
| | Actual addition weight = ±5.0% of the calculated target |
| PAAm-PAA concentration | 0.07 w/w% solids ± 5.0% of nominal |
| $NaH_2PO_4 \cdot H_2O$ | 0.044% (w/w) ± 0.5% of nominal |
| $Na_2HPO_4 \cdot 2H_2O$ | 0.388% (w/w) ± 0.5% of nominal |
| NaCl | 0.79% (w/w) ± 0.5% of nominal |
| NaOH or HCl | To achieve target pH |
| Hydrogen peroxide | 6 ± 1 ppm (peroxide added after heat pretreatment) |
| DI water | q.s. to 100% to account for differences in the PAE target. |
| | (+/- 0.5% of calculated target) |
| Initial pH (prior to pre-reaction) and final pH | 7.4 ± 0.2 |

What is claimed is:

1. A method for making a soft contact lens capable of releasing phosphatidylcholine nanoparticles comprising the steps of:
   a) providing a phosphatidylcholine,
   b) mixing the phosphatidylcholine with an aqueous solution having a pH of 1 to 4 to form a mixture, wherein the aqueous solution is free of an organic solvent,
   c) high-energy treating the mixture of step b) to form a phosphatidylcholine nanoparticle in the mixture with a first concentration,
   d) diluting the mixture of step c) with a buffered saline solution to form a packaging solution, wherein the packaging solution has phosphatidylcholine nanoparticle with a second concentration, wherein the first concentration of the phosphatidylcholine nanoparticle is higher than the second concentration of phosphatidylcholine nanoparticle,
   e) packaging a hydrogel contact lens in a container containing the packaging solution,
   f) autoclaving the hydrogel contact lens in the packaging solution to load the phosphatidylcholine nanoparticle into the hydrogel contact lens, wherein the packaging solution has a pH of from about 6.0 to 8.0, an osmolality of from about 200 to about 450 mOsm/kg.

2. The method of claim 1, wherein the aqueous solution is a de-ionized water or a buffered saline.

3. The method of claim 2, wherein the first concentration of a phosphatidylcholiner nanoparticle in step d) is 1000-50000 ppm.

4. The method of claim 1, wherein the second concentration of the phosphatidylcholiner nanoparticle in step e) is 50 ppm-2000 mg/ml.

5. The method of claim 1, wherein the phosphatidylcholine comprises at least one member selected from the group consisting of 1,2-Didecanoyl-sn-glycero-3-phosphocholine (DDPC), 1,2-Dilauroyl-sn-glycero-3-phosphorylcholine (DLPC), Dimyristoylphosphatidylcholine (DMPC), Dipalmitoylphosphatidylcholine (DPPC), 1,2-Distearoyl-sn-glycero-3-phosphocholine (DSPC), 1,2-Dioleoyl-sn-Glycero-3-Phosphocholine (DOPC), 1-palmitoyl-2-oleoyl-sn-glycero-3-phosphocholine (POPC), 1,2-Dierucoyl-sn-Glycero-3-Phosphatidylcholine (DEPC).

6. The method of claim 5, wherein the phosphatidylcholine is Dimyristoylphosphatidylcholine (DMPC) or Dipalmitoylphosphatidylcholine (DPPC).

7. The method of claim 1, wherein the aqueous solution in step of b) having a pH of 1 to 3.

8. The method of claim 1, wherein the aqueous solution in step of b) having a pH of 1 to 2.

9. The method of claim 1, wherein the buffered saline is at least one member selected from the group consisting of Phosphate-buffered saline or Tris-buffered saline.

10. The method of claim 1, wherein high-energy treating is select from the group consisting of a high speed stirring with at least 800 rpm, a high pressure homogenizer or sonicating.

11. The method of claim 1, wherein the hydrogel contact lens is a silicone hydrogel contact lens.

12. The method of claim 11, wherein the hydrogel contact lens has a load of phosphatidylcholine nanoparticle from 10 μg/lens to 100 μg/lens.

13. The method of claim 11, wherein the hydrogel contact lens has a load of phosphatidylcholine nanoparticle from 20 μg/lens to 80 μg/lens.

* * * * *